(12) United States Patent
Bolz et al.

(10) Patent No.: US 12,023,494 B2
(45) Date of Patent: Jul. 2, 2024

(54) DEVICE FOR PERFORMING A tVNS TREATMENT

(71) Applicant: tVNS Technologies GmbH, Erlangen (DE)

(72) Inventors: Armin Bolz, Buckenhof (DE); Klaus Karg, Schwabach Wolkersdorf (DE)

(73) Assignee: TVNS TECHNOLOGIES GMBH, Erlangen (DE)

( * ) Notice: Subject to any disclaimer, the term of this patent is extended or adjusted under 35 U.S.C. 154(b) by 110 days.

(21) Appl. No.: 16/987,894

(22) Filed: Aug. 7, 2020

(65) Prior Publication Data

US 2021/0038890 A1    Feb. 11, 2021

(30) Foreign Application Priority Data

Aug. 9, 2019    (DE) ..................... 10 2019 121 528.5

(51) Int. Cl.
| | | |
|---|---|---|
| *A61N 1/36* | (2006.01) | |
| *A61N 1/02* | (2006.01) | |
| *A61N 1/04* | (2006.01) | |
| *A61B 5/00* | (2006.01) | |
| *A61B 5/08* | (2006.01) | |
| *A61B 5/11* | (2006.01) | |
| *A61B 5/369* | (2021.01) | |

(52) U.S. Cl.
CPC ......... *A61N 1/36025* (2013.01); *A61N 1/025* (2013.01); *A61N 1/0456* (2013.01); *A61N 1/36031* (2017.08); *A61N 1/36034* (2017.08); *A61B 5/08* (2013.01); *A61B 5/11* (2013.01); *A61B 5/369* (2021.01); *A61B 5/4029* (2013.01)

(58) Field of Classification Search
CPC .. A61N 1/36025; A61N 1/025; A61N 1/0456; A61N 1/36031; A61N 1/36034; A61N 1/36053; A61N 1/36114; A61N 1/36014; A61B 5/08; A61B 5/11; A61B 5/369; A61B 5/4029; A61B 5/0531; A61B 5/4035; A61B 2560/0242; A61B 5/0245; A61B 5/0816; A61B 5/4836
See application file for complete search history.

(56) References Cited

U.S. PATENT DOCUMENTS

| | | | |
|---|---|---|---|
| 2013/0066392 A1* | 3/2013 | Simon | A61N 2/006 607/45 |
| 2015/0142082 A1* | 5/2015 | Simon | A61N 1/36132 607/61 |
| 2016/0279024 A1* | 9/2016 | Hyde | A61N 1/0456 |
| 2017/0224990 A1* | 8/2017 | Goldwasser | A61N 1/0476 |
| 2017/0361089 A1* | 12/2017 | Boggs, II | A61N 1/36017 |
| 2018/0085055 A1* | 3/2018 | Annoni | A61B 5/7475 |
| 2018/0168905 A1* | 6/2018 | Goodall | A61B 5/1124 |
| 2019/0054296 A1* | 2/2019 | Giarola | A61N 1/00 |

FOREIGN PATENT DOCUMENTS

| | | |
|---|---|---|
| DE | 10 2006 023 824 A1 | 11/2007 |
| DE | 10 2010 022 030 A1 | 12/2011 |
| DE | 10 2015 007 215 B3 | 2/2016 |

* cited by examiner

*Primary Examiner* — Amanda K Hulbert
*Assistant Examiner* — Natasha Patel
(74) *Attorney, Agent, or Firm* — McCoy Russell LLP

(57) ABSTRACT

The present invention relates to a device for performing a tVNS treatment having at least one electrode for generating a stimulation pulse, with the device having at least one detection means that is configured to detect one or more parameter values, and with the device having a control or regulation unit that is suitable to set one or more parameters of the stimulation pulse delivered by the electrode in dependence on the detected parameter value or values.

8 Claims, No Drawings

DEVICE FOR PERFORMING A tVNS TREATMENT

BACKGROUND OF THE INVENTION

The present invention relates to a device for performing a tVNS treatment in accordance with the description herein.

So-called transcutaneous vagus nerve stimulation (also called tVNS in the following) is known from the prior art as a treatment method that is based on a branch of the vagus nerve, namely the Ramus auricularis nervi vagi (RANV), being transcutaneously stimulated by electrical pulses. The method is used, for example, in the treatment of medically refractive epilepsy (MRE) and refractive depression.

The treatment is carried out with a device that generates electrical pulses that are delivered through the skin to said branch of the vagus nerve by an ear electrode that is worn like an earphone.

It is known from the prior art that the process of tVNS runs in accordance with a fixed stimulation protocol.

The device works through this stimulation protocol, that is stored in a memory, with fixed parameters after the switching on.

This procedure is inflexible to the extent that the device cannot carry out any adaptation to the current state of the patient or even be synchronized with the physiological rhythm of the patient.

SUMMARY OF THE INVENTION

It is therefore the underlying object of the invention to further develop a device of the initially named kind such that it enables an improved treatment with respect to conventional devices.

This object is achieved by a device having the features herein.

Provision is accordingly made that the device for performing a tVNS treatment is configured with at least one electrode for generating a stimulation pulse, with the device having at least one detection means that is configured to detect one or more parameter values, with the device having a control or regulation unit that is suitable to set one or more parameters of the stimulation pulse delivered by the electrode in dependence on the detected parameter value or values.

Differing from (non-adaptive) tVNS devices known from the prior art, it is thus not always the same stimulation that is performed. With respect to one or more parameters such as the duration or strength of the pulse, it is rather dependent on one or more parameter values that are measured by a sensor system, i.e. by the detection means.

The key advantage can thus be achieved that the stimulation and thus also the success of the treatment can take place in a manner individual to the patient or that parameters that may influence the stimulation such as room temperature, etc. can enter into the stimulation, which increases the success of the treatment with respect to an inflexible stimulation routine, i.e. stimulation protocol.

The detection means are preferably configured in the form of one or more sensors.

The detection means can be configured to measure the parameter value or values such as the heart rate of the patient in real time and the control or regulation unit can be configured to set the stimulation pulse in dependence on the parameter value or values measured in real time. In this case, the storage of the measured parameter value is not absolutely necessary. The (non-stored) heart rate e.g. rather serves as an input value on the basis of which the stimulation pulse is then set.

Provision is made in a further embodiment that the detection means are connected to a memory such that the parameter values measured by the detection means are stored in the memory and such that the control or regulation unit is configured to set the stimulation pulse in dependence on the parameter value or values stored in the memory.

It would, for example, be conceivable that the heart rate is determined and stored over a longer time period and that the stimulation pulse is delivered on the basis of the stored values.

The kind of parameters measured by detection means is as desired.

They can be vital parameters or patient parameters or external parameters that have no relation to the patient.

By way of example, the patient parameter or parameters can be the heart rate of the patient, at least one parameter that can be determined by means of an EEG sensor, a parameter relating to breathing, or a parameter relating to the sympathovagal balance, or a parameter relating to the movement of the patient, or a combination of the aforesaid parameters.

As stated, alternatively or additionally, no parameters relating to the patient can enter into the control or regulation of the stimulation pulse such as the room temperature, the air pressure, or other external physical variables, i.e. physical variables not specific to the patient.

A closed-loop control, i.e. a feedback control, is also conceivable and covered by the invention.

It is thus conceivable, for example, that the regulation unit is configured to control the electrode such that the parameter value detected by means of the detection means is adjusted to a desired value or to a desired value range by means of the stimulation pulse. By way of example, an embodiment cold be configured such that tVNS influences the autonomous tone, i.e. the sympathovagal balance. If this tone is detected e.g. via pupillometry or skin conductivity sensors, the regulation unit can be configured such that it specifically influences the stimulation and thus adapts the tone to the current requirement in the form of a desired value or a desired value range.

In a further embodiment of the invention, the control or regulation unit is configured to coordinate the stimulation pulse or pulses with periodically occurring physiological processes, in particular neurological processes, of the patient.

It is thus conceivable, for example, that the detection means are suitable to detect the breathing of the patient and that the control or regulation unit is configured to coordinate the stimulation pulses with the breathing signal or to trigger them.

Provision can be made in accordance with a method for the device for performing a tVNS treatment that a stimulation pulse is generated by means of at least one electrode, preferably by means of an ear electrode, with one or more parameter values being detected in advance and with one or more parameters of the stimulation pulse delivered by the electrode being set by a control or regulation unit in dependence on the parameter value or values.

DESCRIPTION OF THE PREFERRED EMBODIMENTS

Preferred features of the method can be found in the description herein.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment described in the following.

The embodiment relates to a device for performing a tVNS treatment that has one or more electrodes, preferably ear electrodes, for delivering stimulation pulses.

The vagus stimulation is based on a branch of the vagus nerve in the form of the Ramus auricularis nervi vagi (RANV) sensitively supplying the skin of the auricle in the region of the concha.

The RANV can be stimulated transcutaneously, that is through the skin, with electrical pulses by means of the electrode. The stimulation of the RANV causes an excitation of the vagus nerve that, as in conventional (non-transcutaneous) VNS, enters into the more highly disposed centers of the brain via the brainstem.

The device generates electrical pulses and can have the size of a smartphone.

One or two ear electrodes can be used. The electrodes deliver the pulses through the skin to the branch of the vagus nerve. The ear electrodes can be configured such that they have loudspeakers so that the patient can hear music or the like during the treatment.

Unlike a known device for performing a tVNS, the device in accordance with the invention is a device for adaptive tVNS, i.e. a device whose stimulation protocol is not always identical, but rather depends on one or more parameters specific to the patient and/or one or more parameters not specific to the patient.

The basic idea of the present invention thus comprises the expansion of a conventional tVNS stimulation device by various sensors that serve the control or variation of the stimulation parameters.

The response to an event is named as a first embodiment.

It is thus known that the heart rate of the patient increases briefly before an epileptic fit. The stimulation unit in accordance with the invention is able to monitor the progression of the heart rate and to adapt its stimulation to the current heart rate via an ECG sensor.

The synchronization of the delivered pulses with periodically occurring processes of the patient is named as a second embodiment.

Certain neurological processes are subject to a certain periodicity. The tVNS device in accordance with the invention can thus, for example, be synchronized to the physiological rhythm by means of an EEG sensor and can thus dramatically improve the therapeutic effect because it always treats in the sensitive phase of the patient.

In a further example, the detection means is a breathing sensor that is configured to measure the periodic state of the sympathovagal system. The breathing sensor communicates the periodic state of the sympathovagal system and the tVNS device in accordance with the invention triggers in response to this breathing signal.

In a further example, a closes loop embodiment is conceivable, i.e. a regulation of a parameter to a desired value or in a desired value range.

By way of example, it can be named as an example for this that the tVNS influences the autonomous tone, more exactly the sympathovagal balance. If this tone is detected, for example, via pupillometry or skin conductivity sensors, the stimulation can be specifically influenced and can thus be adapted to the current need of the patient. The tone can be maintained in a specific desired value range individual to the patient in this manner, with the stimulation pulse or pulses serving as an "actuator".

It is pointed out that the aforesaid embodiments do not restrict the invention. A plurality of sensors is generally conceivable. All the vital parameters are generally suitable, but also external physical variables such as movement, temperature, or pressure.

The invention claimed is:

1. A device for performing a tVNS (transcutaneous vagus nerve stimulation) treatment having at least one electrode for generating a stimulation pulse, wherein
   the device has detection means configured to detect one or more parameter values, and
   a control or regulation unit configured to set one or more parameters of the stimulation pulse delivered by the electrode in dependence on the detected one or more parameter values,
   the detection means are configured to measure the one or more parameter values in real time,
   the control or regulation unit is configured to set the stimulation pulse in dependence on the one or more parameter values measured in real time,
   the detection means comprise pupillometry and/or skin conductivity sensors,
   the control or regulation unit is configured to influence sympathovagal balance based on tone detected by said sensors,
   the device comprises a closed loop to regulate the tone to a desired value or range, and
   the detection means comprise a breathing and/or movement sensor configured to detect and communicate periodic state of a sympathovagal system to the control or regulation unit which is configured to trigger the device in response to a breathing signal and/or a signal relating to the movement of the patient from the detection means.

2. A device in accordance with claim 1, wherein the control or regulation unit is configured to coordinate the stimulation pulses with periodically occurring physiological processes of the patient.

3. A device in accordance with claim 2, wherein the physiological processes are neurological processes.

4. A device in accordance with claim 1, wherein the electrode is an ear electrode.

5. A device in accordance with claim 4, wherein the electrode comprises a loudspeaker.

6. A device in accordance with claim 1, wherein the detection means comprise an EEG and/or ECG sensor.

7. A device in accordance with claim 1, wherein the measured one or more parameter values are added to an inflexible stimulation routine.

8. A device in accordance with claim 1, wherein the one or more parameter values are not stored in the device when measured in real time.

* * * * *